United States Patent [19]

Nagai et al.

[11] Patent Number: 5,142,028
[45] Date of Patent: Aug. 25, 1992

[54] MONOCLONAL ANTIBODIES CAPABLE OF RECOGNIZING GANGLIOSIDES $GQ_{1b}$ AND $GT_{1a}$

[75] Inventors: Yoshitaka Nagai, Tokyo; Hideki Yamamoto, Kawasaki; Kinji Takada, Tokyo; Masayoshi Ito, Kunitachi, all of Japan

[73] Assignee: Mect Corporation, Tokyo, Japan

[21] Appl. No.: 377,121

[22] Filed: Jul. 10, 1989

[30] Foreign Application Priority Data

Jul. 16, 1988 [JP] Japan .................................. 63-177582

[51] Int. Cl.⁵ .......................... C07K 15/28; C12N 5/18; C12N 15/02
[52] U.S. Cl. .............................. 530/387.5; 530/388.2; 435/240.27; 435/172.2
[58] Field of Search .................... 530/387; 435/240.27, 435/172.2; 935/104

[56] References Cited

PUBLICATIONS

Kasai et al., Brain Res., 277:155–158, 1983.
Biological Abstracts, vol. 77, No. 10, 1984, abstract No. 77313, Philadelphia, Pa., US; S. K. Kundu et al.: "Binding of Monoclonal Antibody A2B5 to Gangliosides". Biochem. Biophys. Res. Commun. 116(3), 836–842, 1983.
J. Exp. Med. The Rockefeller University Press, vol. 150, Oct. 1979, 1008–1019.
Eur. J. Immunol. 1986, 16: 951–956, Thomas Brodin et al.

Primary Examiner—John J. Doll
Assistant Examiner—Susan L. Futrovsky
Attorney, Agent, or Firm—Oblon, Spivak, McClelland, Maier & Neustadt

[57] ABSTRACT

A monoclonal antibody specifically recognizes an epitope or an antigenic determinant represented by the following formula and specifically reacts therewith:

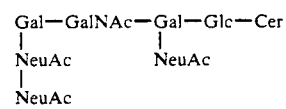

The monoclonal antibody can be obtained by cultivating hybridoma cells which can be generated by a method comprising cell-fusing (A) B cells or lymphocytes obtained by immunizing an animal with a substance involving the epitope or the antigenic determinant represented by the foregoing formula and (B) myeloma cells. The monoclonal antibody shows high specificity to ganglioside $GQ_{1b}$ and ganglioside $GT_{1a}$ having a specific epitope and thus can detect the epitope in high sensitivity. Therefore, the antibody can be used for the elucidation of sugar chain's roles in cell functions and for studying the development of animals. Moreover, the monoclonal antibody would have various clinical applications.

5 Claims, 1 Drawing Sheet

RESORCINOL STAINING

RESORCINOL STAINING

IMMUNOSTAINING

MONOCLONAL ANTIBODIES CAPABLE OF RECOGNIZING GANGLIOSIDES $GQ_{1b}$ AND $GT_{1a}$

BACKGROUND OF THE INVENTION

1. Field of the Invention

The present invention relates to novel anti-ganglioside glycolipid monoclonal antibodies and more specifically to monoclonal antibodies capable of recognizing gangliosides $GQ_{1b}$ and $GT_{1a}$ and a novel hybridoma which produces such monoclonal antibodies as well as a method for generating the hybridoma.

2. Description of the Prior Art

In 1975, Kohlor et al. developed a hybridoma which produces an anti-sheep red blood cell antibody and which is generated by fusing spleen cells derived from an immunized animal and mouse myeloma cells. A clone which is a hybridoma originated from a single cell can be isolated from such hybridoma cells (so-called "cloning") because of its high proliferation potency. All the antibodies produced by such a cloned hybridoma are identical with each other and their antigen-recognizing sites are also identical. Therefore, they have identical specificity to a specific antigen. In addition, the stable supply of such a monoclonal antibody can be ensured since the hybridoma cells can be stored in the frozen state, for instance, in liquid nitrogen.

Conventional anti-sera have been prepared by letting the serum from an immunized animal absorb a variety of antigens. Therefore, they contain a large number of antibody molecules originated from different B cells (polyclonal) and hence often cause cross reactions with other antibodies. Thus, it is difficult to obtain anti-sera exhibiting excellent specificity according to such methods. However, the foregoing cell fusion technique permits the production of monoclonal antibodies which can specifically react with a specific antigen.

Antibodies are proteins which can recognize a molecule known as the "antigen" inherent thereto and can be bound to the same. The monoclonal antibody is an antibody having a single antigen-recognizing site and hence recognizes only one kind of antigenic determinant. Various techniques for producing monoclonal antibodies and those for generating hybridomas capable of producing the same are detailed in "Monoclonal Hybridoma Antibodies: Techniques and Applications", edited by John G. Hurrell, 1983.

The glycolipids of mammalian cells belong to the category of so-called sphingoglycolipids and comprise (i) a lipid structure referred to as ceramide composed of a long-chain aminoalcohol called sphingosine to which a fatty acid is acid amido-bound and (ii) various combination of sugars selected from the group consisting of glucose, galactose, N-acetylglucosamine, N-acetylgalactosamine, fucose and sialic acid which are bonded to the structure through glycoside bonds. Among these, the glycolipids carrying sialic acid are, in particular, referred to as "gangliosides".

These compounds are generally located in the outer molecular layer of the two-molecular-layer structure of lipids of cell membrane and it has been thought, from recent investigations, that the compounds play an important role in the functions such as a reception of information for discrimination in the cells and response to such information; receptor functions; differentiation; and proliferation, malignant change, behaviors or the like of cells.

Among these gangliosides, ganglioside $GQ_{1b}$ can be considered to be a marker of a certain kind for the growth, differentiation or the like of nerve cells.

Therefore, the development of monoclonal antibodies specific to gangliosides $GQ_{1b}$ and $GT_{1a}$ have been an important subject for the elucidation of sugar chain's roles in cell functions and for studying the development of animals, since the monoclonal antibody has high specificity to a specific antigen and thus can detect the same in high sensitivity.

SUMMARY OF THE INVENTION

Accordingly, an object of the present invention is to provide a novel monoclonal antibody having specificity to gangliosides $GQ_{1b}$ and $GT_{1a}$ which are identified to be a marker for the growth and differentiation of nerve cells.

Another object of the present invention is to provide a hybridoma capable of producing a monoclonal antibody specific to ganglioside $GQ_{1b}$ and $GT_{1a}$ in a high yield.

A further object of the present invention is to provide a method for producing a hybridoma capable of producing such a monoclonal antibody.

The inventors of this invention have conducted various studies to achieve the foregoing objects, have found that an anti-$GQ_{1b}$ ganglioside monoclonal antibody produced through the use of purified $GQ_{1b}$ ganglioside as an immunogen exhibits high specificity to an epitope (or an antigenic determinant) and thus have completed the present invention.

Consequently, the present invention provides a novel monoclonal antibody having specificity to gangliosides $GQ_{1b}$ and $GT_{1a}$ involving an epitope (or an antigenic determinant) represented by the following formula:

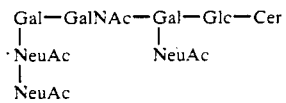

Wherein Gal represents galactose; GalNAc represents N-acetylgalactosamine; Glc represents glucose; Cer represents ceramide; and NeuAc represents an acetyl neuraminate residue.

According to another aspect of the present invention, there is provided a novel hybridoma (ATCC HB9714) which produces a novel monoclonal antibody having specificity to gangliosides $GQ_{1b}$ and $GT_{1a}$ involving an epitope (or an antigenic determinant) represented by the following formula:

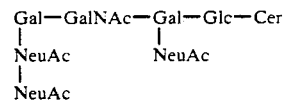

The hybridoma of the present invention was deposited with the American Type Culture Collection, Rockville, Md., under accession no. HB 9714.

According to a further aspect of the present invention there is provided a method for generating the aforementioned hybridoma which is characterized by fusing (A) B cells (B lymphocytes) obtained by immunizing an animal with a ganglioside glycolipid involving an epitope (or an antigenic determinant) represented by the following formula:

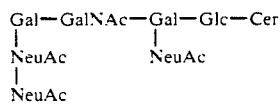

and (B) myeloma cells.

DETAILED EXPLANATION OF THE INVENTION

Figure 1A:
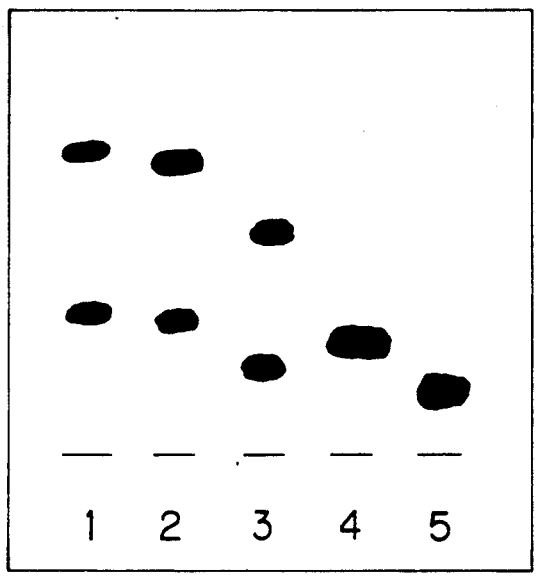
FIG. 1(A) shows the results of qualitative tests on a variety of gangliosides obtained by TLC resorcinol staining technique.

The present invention will hereinunder be explained in more detail.

The hybridoma of the present invention can be produced according to the method of Kohlor and Millstein et al., more specifically a method which comprises cell-fusing B cells (B lymphocytes) derived from an animal immunized with an antigen and myeloma cells.

Gangliosides $GQ_{1b}$ and $GT_{1a}$ which involve the epitope specific to the monoclonal antibody of this invention have the following structural formulas:

(A) $GQ_{1b}$: 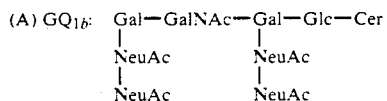

(B) $GT_{1a}$: 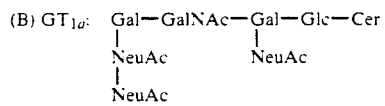

Examples of ganglioside glycolipids which do not exhibit any specific reactivity with the monoclonal antibody of this invention will be listed below:

(C) $GD_3$: 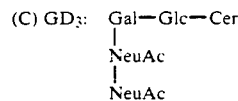

(D) $GM_3$: 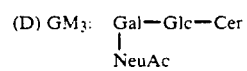

(E) $GM_2$ 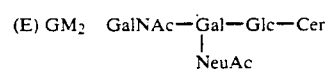

(F) $GD_{1a}$: 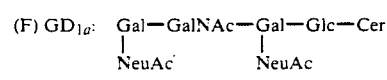

(G) $GT_{1b}$: 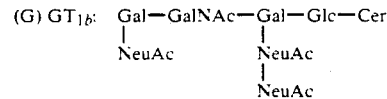

-continued (H) $GD_{1b}$: 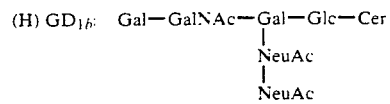

The monoclonal antibody according to the present invention can recognize the compound having the following structural formula:

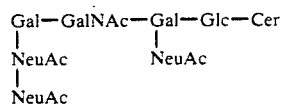

as an epitope and specifically reacts therewith. Therefore, the monoclonal antibody of the present invention shows particularly strong specificity to ganglioside glycolipids involving the foregoing antigenic determinant, in particular, ganglioside $GQ_{1b}$ and ganglioside $GT_{1a}$. Moreover, the kinds of animals from which the ganglioside glycolipids are derived are not restricted to specific ones so far as the gangliosides have the aforesaid antigenic determinant and such gangliosides exhibit similar specificity to the monoclonal antibody according to the present invention.

The monoclonal antibodies of this invention can be produced by hybridoma cells obtained by fusing B cells and myeloma cells.

Referring first to "animals" which can be immunized with the aforementioned ganglioside glycolipids as antigens, examples thereof used include almost all the animals such as rabbits, mice and rats and preferred are mice, in particular, Balb/c mice. The B cells (B lymphocytes) thus obtained are those capable of producing monoclonal antibody of the present invention and preferably used are spleen cells.

On the other hand, the "myeloma cells" used in such cell fusion embrace those originated from almost all the kinds of animals such as human beings, mice, rats and rabbits and preferred are those derived from mice, in particular, X63-Ag 8.653 myeloma cells derived from Balb/c mice. These myeloma cells have an ability of active proliferation (high proliferation potency) and hence they can impart vigorous proliferation potency to the hybridoma cells of the present invention which can be obtained through the cell-fusion of the myeloma cells with the foregoing B cells.

The method for generating the hybridoma cells of the present invention will be described in more detail below.

First of all, ganglioside $GQ_{1b}$ is injected into mice intraperitonealy, subctaneously or intravenously, preferably intravenously. In general, an adjuvant, in other words an agent for immunological enhancement is used simultaneously and it may be either complete or incomplete adjuvants. For instance, such adjuvants include oils, emulsifying agents, inactivated or killed tubercule bacillus cells, inactivated or killed Salmonella cells and a mixture thereof, preferably inactivated or killed Salmonella minesota cells for intraperitoneal and subcutaneous administration and for intravenous injection. In addition, these antigens and adjuvants are preferably used in the form of a solution having approximately physiologically acceptable composition such as a solution in phosphate buffered physiological saline (PBS).

In this immunization, it should be noted that it is difficult to sensitize an animal to be immunized with the self-components and thus it is preferred, in principle, to select the animal phenogenetically distant from the animal from which the antigenic substance is obtained. In order to avoid such difficulties, the immunization can also be performed in vitro.

Then, the B cells and the myeloma cells thus obtained are fused together. As an agent for cell fusion, there can be used polyethylene glycol and HVJ, preferably polyethylene glycol 6,000. In addition, it is preferred to use HAT medium as the culture medium whereby the resulting hybridoma cells can easily be separated from the myeloma cells which remain un-fused.

Thereafter, the resultant hybridoma cells are subjected to cloning operation such as methylcellulose technique, soft agarose technique or limiting dilution technique to isolate a desired single cloned hybridoma. The objective monoclonal antibodies can be obtained from the hybridoma thus isolated.

The antibody titer of the monoclonal antibody can be examined in an ordinary manner to select hybridoma exhibiting high antibody titer for producing hybridoma thus generated. The hybridoma thus selected is then stored as already explained above.

The monoclonal antibody according to the present invention shows high specificity to ganglioside $GQ_{1b}$ and ganglioside $GT_{1a}$ having the specific epitope and thus can detect the epitope in high sensitivity. Therefore, the antibody of this invention can be used for the elucidation of sugar chain's roles in cell functions and for studying the development of animals. Moreover, the monoclonal antibody would have clinical applications.

The present invention will hereunder be described in more detail with reference to the following working Examples, but it is noted that the present invention is not restricted to these specific Examples.

EXAMPLE

(A) Preparation of Samples (1) Extraction and Purification of Gangliosides $GD_3$, $GM_3$ and $GT_{1a}$ and Preparation of Other Gangliosides After hog adrenal was homogenized in cold acetone and was dried, the dried product was extracted with chloroform-methanol in an ordinary manner.

The resultant sample was treated with an alkali and then ganglioside $GD_3$ was purified utilizing DEAE-Sephadex A-25 anion exchange resin and Iatrobeads column.

Ganglioside $GM_3$ was prepared by centrifuging dog serum treated with heparin, washing the resultant sediment three times with phosphate-buffered saline [PBS(−)], lyophilizing it and then subjecting the product to extraction with chloroform-methanol. The purification of ganglioside $GM_3$ was performed according in the same manner as in the purification of ganglioside $GD_3$.

According to the same procedures as in the preparation of ganglioside $GD_3$, purified ganglioside $GT_{1a}$ was obtained from bovine encephalon.

Gangliosides $GD_{1a}$, $GD_{1b}$ and $GQ_{1b}$ were available from DAIATRON CO., LTD.; and gangliosides $GT_{1b}$ and $GM_2$ from FUNAKOSHI Company and these gangliosides were used without further purification.

These ganglioside glycolipids were dissolved in chloroform-methanol [1:1 (v/v)] mixture or ethanol and stored at −20° C.

(2) Test Animals

Six female Balb/c mice of 6-week-old were used for experiments after breeding under ordinary conditions.

(3) Preparation of Antigen Solution

The antigen solution used in the following experiments was prepared by admixing 100 μg of ganglioside $GQ_{1b}$ and 1,000 μg of Salmonella minesota·Rm595 treated with acetic acid as an adjuvant in 1 ml of phosphate-buffered saline [PBS(−)] from which Ca and Mg had been removed.

(4) Culture Medium

Culture Medium: Nissui ②  RPMI-1640 (available from Nissui Pharmaceutical Co. Ltd.) was used. To the medium, there were added kanamycin sulfate and fetal bovine serum (FBS) so that the final concentrations thereof were equal to 50 μg/ml and 10% respectively, prior to use.

HAT Medium: 0.0388 g of thymidine and 0.1361 g of hypoxanthine were dissolved in 100 ml of distilled water under heating and the resulting solution (a) was stored at −20° C. as a stock solution having a concentration 100 times higher than the desired one. Likewise, 0.0176 g of aminopterin was dissolved in 100 ml of distilled water to which a small amount of 1N aqueous solution of sodium hydroxide had been added, then this was diluted 10 times with RPMI-1640 culture medium and the resultant solution (b) was stored at −20° C. as a stock solution having a concentration 100 times higher than the desired one while shielding the light. HAT medium was prepared by adding 1/100 volume each of these two solutions to RPMI-1640 culture medium containing 10% FBS immediately before use.

HT Medium: This was prepared by simply adding 1/100 volume of the stock solution (a) containing hypoxanthin and thymidine to the same RPMI-1640 culture mesium containing 10% FBS.

(5) Parent Cells

As the parent cells for cell fusion, there was used myeloma cells (SP 2/0-Ag 14 cells) which were derived from Balb/c mice. These cells were subjected to subculture in RPMI-1640 culture medium containing 10% FBS while the generation of mutant was inhibited by adding 6-thioguanine to the medium so that its concentration was equal to 3 μg/ml.

(B) Generation of Hybridoma (1) Method of Immunization

Female Balb/c mice of 6-week-old were immunized by intravenously injecting the antigen solution prepared above as an immunogen in accordance with the following immunization schedule (the amount injected was expressed in the amount of ganglioside $GQ_{1b}$): 5 μg at initial; 5 μg day 8 after the initial immunization; and 5 μg day 22 thereafter. 4 Days after the final immunization, the mice were sacrificed to dissect away the spleen thereof and a suspension in which spleen cells were separately dispersed was prepared therefrom to use the same in cell fusion.

(2) Cell Fusion

Fusion of the spleen cells (lymphocytes) with and the mouse myeloma cells, i.e., the foregoing parent cells, was performed according to the method of Kohlor and Millstein. More specifically, $1 \times 10^8$ spleen lymphocytes were fused with $2 \times 10^7$ mouse myeloma cells in the presence of 50% polyethylene glycol (PEG 6000) in a culture medium.

(3) Selection and Breeding of Hybridoma

After the cell fusion procedure, the resultant cells were cultured in HAT culture medium 37° C. in the presence of 5% $CO_2$.

The resultant culture broth of the grown hybridoma cells was examined on whether the hybridoma cells can produced antibodies specific to ganglioside $GQ_{1b}$ or not, by enzyme-labeled antibody technique. Then the hybridoma in the well, in which the desired antibody has been detected antibody-producing cell line was cloned. The hybridoma thus generated was deposited with American Type Culture Collection (ATCC) under the accession number of HB 9714. The monoclonal antibody in the hybridoma culture was inspected on the following points.

(C) Estimation of the Reactivity of the Monoclonal Antibody with Gangliosides (1) Enzyme-Linked Immuno Absorbent Assay (ELISA Method)

96-Well flat-bottomed plate (available from Falcon Co., Ltd.) was pretreated with ethanol before using in experiments. 50 μl each of the antigen solution which had been diluted with ethanol to adjust the concentration of ganglioside $GQ_{1b}$ to 20 μg/ml (optimum concentration) was pipetted into wells of the plate, then the solvent was evaporated off therefrom, 100 μl each of 1% ovalbumin solution in PBS (−) was introduced into the wells and they were allowed to stand for 30 minutes at room temperature. The plate was shaken while it was upside down to remove the solution, then 50 μl each of the supernatant of the hybridoma culture broth, as the primary antibody, was added and the plate was allowed to stand for 1.5 hours at room temperature. Likewise, the primary antibody was removed from the wells, then the wells were washed three times by adding 150 μl of PBS (−) solution and was allowed to stand for 30 minutes at room temperature after the addition of 100 μl each of 1% ovalbumin solution in PBS (−). After the removal of this solution, 50 μl each of a secondary antibody diluted with 1% ovalbumin solution in PBS (−) to its optimum concentration was added and was allowed to stand for 1.5 hours at room temperature. As in the case of the primary antibody, the wells were washed three times with PBS (−) solution and 100 μl each of a reaction solution was added to the wells to cause reaction in the dark. The reaction solution was prepared by dissolving, into citrate-phosphate buffer (pH=5), o-phenylenediamine and hydrogen peroxide so that the concentrations thereof were 0.4 mg/ml and 0.01%, respectively. The reaction was stopped by the addition of 30 μl each of 8N sulfuric acid solution and then the product was examined by colorimetry at 500 nm. As the second antibody, there were used goat anti-mouse IgG, M and A antibodies conjugated with horseradish peroxidase (HRP). The results obtained are summarized in the following Table I.

As seen from the results listed in Table I, the monoclonal antibody according to the present invention certainly recognizes ganglioside $GQ_{1b}$.

Moreover, the supernatant of the hybridoma culture broth was diluted to obtain a primary antibody and an antigen-antibody reaction was carried out using the primary antibody. The results thus obtained are listed in the following Table II. The results listed in Table II clearly indicate that the monoclonal antibody of the present invention has reactivity to ganglioside $GQ_{1b}$.

TABLE 1

| Antigen $GQ_{1b}$ pmol/well | Optical Density at 500 nm Hybridoma Culture Broth |
|---|---|
| 100 | 1.477 ± 0.011 |
| 50 | 1.502 ± 0.018 |
| 25 | 1.399 ± 0.076 |
| 10 | 0.853 ± 0.099 |
| 5 | 0.621 ± 0.063 |
| 2.5 | 0.486 ± 0.058 |
| 1 | 0.380 ± 0.042 |
| 0.5 | 0.317 ± 0.043 |
| 0.25 | 0.233 ± 0.048 |
| 0 | 0.141 ± 0.028 |

Triplicate Test
Secondary antibody Dilution
(× 2500; with 1% BSA PBS (−))

TABLE II

| Primary Antibody Dilution (1% BSA PBS (−)) | Optical Density at 500 nm Antigen $GQ_{1b}$ 100 pmole/well |
|---|---|
| × 1 | 1.477 ± 0.011 |
| × 2 | 1.323 ± 0.134 |
| × $2^2$ | 0.957 ± 0.093 |
| × $2^3$ | 0.444 ± 0.121 |
| × $2^4$ | 0.223 ± 0.032 |
| × $2^5$ | 0.154 ± 0.005 |
| × $2^6$ | 0.075 ± 0.056 |
| × $2^7$ | 0.075 ± 0.054 |

Triplicate Test
Secondary antibody Dilution
(× 2500; with 1% BSA PBS (−))

(2) TLC Immunostaining Technique

A silica gel thin layer chromatographic plate [TLC (POLY GRAM SIL G)] was cut into pieces of appropriate size and was spotted with a small drop of the solution of a glycolipid in chloroform-methanol (1:1 (v/v)). Depending on purposes, the plate was developed with a developing solution such as chloroform-methanol-water (60/40/10; v/v), chloroform-methanol-0.5% $CaCl_2$ solution (55/45/10; v/v) or chloroform-methanol-2.5N $NH_4OH$ solution (60/40/9; v/v) and then was allowed to stand in 1% ovalbumin-1% polyvinyl pyrrolidone (K-30)-PBS (−) solution at 4° C. over night. Then, it was shaken for 2 hours at room temperature while dipping it in the primary antibody solution. After sufficiently washing with PBS (−) solution, it was dipped in 1% ovalbumin-1% polyvinyl pyrrolidone (K-30)-PBS (−) solution at room temperature for 30 minutes. The plate was withdrawn therefrom, was dipped, for 2 hours, in the secondary antibody which was diluted to its optimum concentration with 3% polyvinyl pyrrolidone (K-30) solution in PBS (−) with shaking, then sufficiently washed with PBS (−) solution and a reaction solution was added thereto. The reaction solution was prepared by dissolving 4 mg of 4-chloro-1-naphthol in 1 ml of methanol, adding 50 mmole of tris(hydroxymethyl)-aminomethane, 200 mmole of NaCl and 5 ml of a buffer (pH=7.4) and then adding hydrogen peroxide so that the concentration thereof was 0.01%. The reaction was stopped by washing the plate and then air-dried. The results obtained are summarized in the following Table III.

TABLE III

| Antigen (100 pmole) | Antibody (area of peak) |
| --- | --- |
| GM3 | N.D. |
| GM2 | N.D. |
| GD3 | N.D. |
| GD1a* | N.D. |
| GD1b* | N.D. |
| GT1b | N.D. |
| GQ1b | 83,509 |

N.D.: not detected.
GD1a: 50 pmole.
GD1b: 50 pmole.

As seen from the results listed in Table III, the monoclonal antibody according to the present invention specifically reacts with ganglioside $GQ_{1b}$.

Figure 1B:
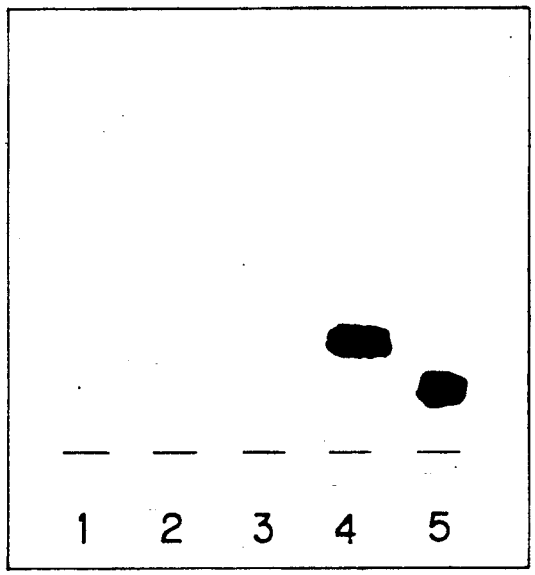
FIG. 1(B) shows the antigen specificity of various kinds of gangliosides to the monoclonal antibody of the present invention determined by TLC immunostaining technique.

(3) Identification of Epitopes Specific to the Monoclonal Antibody of the Present Invention FIG. 1 shows the results of qualitative tests and immunoreactions of various kinds of glycolipids obtained by TLC staining technique (resorcinol staining) (A) and TLC immunostaining technique (B). It is found, from the results shown in FIG. 1, that gangliosides $GT_{1a}$ and $GQ_{1b}$ of lanes 4 and 5 have antigenic determinants specific to the monoclonal antibody of the present invention. The lanes appearing in FIG. 1 are as follows:

| (1) Lane 1 | GM3 | 846 pmole |
| --- | --- | --- |
|  | GD1a | 860 pmole |
| (2) Lane 2 | GD3 | 679 pmole |
| (3) Lane 3 | GD1b | 592 pmole |
|  | GM2 | 1 nmole |
|  | GT1b | 354 pmole |
| (4) Lane 4 | GT1a | 195 pmole |
| (5) Lane 5 | GQ1b | 290 pmole |

What is claimed is:

1. A monoclonal antibody which specifically binds an epitope or an antigenic determinant represented by the following formula:

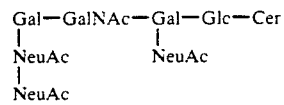

wherein Gal represents galactose; GalNAc represents N-acetylgalactose amine; Glc represents glucose; Cer represents ceramide; and NeuAc represents an acetyl neuraminate residue, and wherein said antibody does not bind gangliosides GD3, GD2, GD1b, and GT1b.

2. The monoclonal antibody which specifically binds to ganglioside glycolipids involving the epitope or antigenic determinant of claim 1.

3. The monoclonal antibody of claim 2 wherein the ganglioside glycolipid is ganglioside $GQ_{1b}$ or ganglioside $GT_{1a}$.

4. A hybridoma capable of producing the monoclonal antibody as set forth in claim 1.

5. The hybridoma of claim 4 wherein it is the hybridoma ATCC HB 9714.